United States Patent [19]

Braun et al.

[11] Patent Number: 5,965,114

[45] Date of Patent: Oct. 12, 1999

[54] DYE-CONTAINING MASS, COMPOSITION CONTAINING IT AND METHOD FOR DYEING KERATIN FIBERS, ESPECIALLY HUMAN HAIR

[75] Inventors: Hans-Jurgen Braun, Ueberstorf; Pascal Andre Semadeni, Cordast, both of Switzerland

[73] Assignee: Wella AG, Darmstadt, Germany

[21] Appl. No.: 08/965,960

[22] Filed: Nov. 7, 1997

[30] Foreign Application Priority Data

Nov. 20, 1996 [DE] Germany ............................ 196 48 019

[51] Int. Cl.⁶ ...................................................... A61K 7/13
[52] U.S. Cl. .................................. 424/70.1; 8/423; 514/27
[58] Field of Search ............................ 424/70.1; 514/27; 8/423

[56] References Cited

U.S. PATENT DOCUMENTS

| | | | |
|---|---|---|---|
| 5,364,767 | 11/1994 | Flowers et al. | 435/39 |
| 5,704,948 | 1/1998 | Terranova et al. | 8/409 |
| 5,792,220 | 9/1998 | Wenke et al. | 8/409 |
| 5,796,903 | 9/1998 | Tran | 358/123 |

Primary Examiner—Jose' G. Dees
Assistant Examiner—Michael A. Williamson
Attorney, Agent, or Firm—Michael J. Striker

[57] ABSTRACT

The dye-containing mass contains or consists of a compound of formula I:

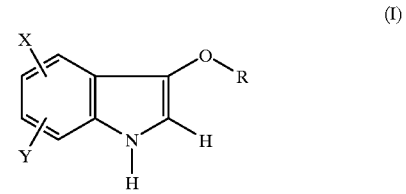

wherein R represents a DL-, D- or L-aldopyranose or a DL-, D- or L-ketopyranose, and X and Y, independently of each other, each represent a hydrogen atom, a halogen atom, a hydroxy group or an alkoxy group with from 1 to 4 carbon atoms; and, if needed, a direct-dyeing dye compound. The ready-to-use hair dye composition according to the invention is obtained by mixing this dye-containing mass with a hydrolase enzyme, e.g. a β-galactosidase. The method for dyeing hair includes applying this ready-to-use hair dye composition to the hair.

12 Claims, No Drawings

DYE-CONTAINING MASS, COMPOSITION CONTAINING IT AND METHOD FOR DYEING KERATIN FIBERS, ESPECIALLY HUMAN HAIR

BACKGROUND OF THE INVENTION

The present invention relates to a dye-containing mass, composition containing it and method for dyeing keratin fibers, especially human hair.

The use of ground plants for dyeing of hair has in principle been known from antiquity. Customarily pulverized or ground plant parts from plants which are most effective for dyeing purposes, such as Indigo leaves or Henna are used, are stirred with water, filler materials and thickeners to form a dye paste and then this dye paste is applied to the hair. This process has however the disadvantage that the dye powder must be ground very fine in order to dye the hair uniformly. Furthermore in many cases the dye does not penetrate into the hair and water-insoluble components remain on the hair which are only washed out of the hair completely with great difficulty. Finely grinding up the dye has the disadvantage that the preparation and processing of it is accompanied by the production of an unpleasant dust. Extraction of natural materials from the appropriate plants and processing the extract to obtain a dye preparation has already been attempted. The dye substances isolated from the plants by extraction are however very unstable to the effects of oxygen and light and are unsuitable for making stable dye compositions.

The Indigofera plants contain Indicane(the dye precursor of Indigo) which can be easily cleaved by hydrolysis into indoxyl and glucose. The indoxyl obtained thereby is converted into Indigo already by action of oxygen. Indigo is a blue dye with good fastness properties and has been used to dye textile materials for a thousand years. Since Indigo is water insoluble however this dye must be converted into a water soluble form(the so-called indigo bath solution) by a reduction process, for example by means of an alkaline hydrogen sulfite solution. A process of this type is however of little practical value for dyeing hair.

SUMMARY OF THE INVENTION

It is an object of the present invention to provide a dye-containing mass for dyeing keratin fibers, especially human hair, based on the use of a suitable indigo precursor compound, which does not have the above-described disadvantages.

It is another object of the present invention to provide a ready-to-use composition and method for dyeing keratin fibers, especially human hair, based on the use of the indigo precursor compound, which does not have the above-described disadvantages.

It has now been surprisingly found that blue hair dye compounds can be obtained which do not have the above-described disadvantages using a suitable Indigo precursor compound according to formula I presented hereinbelow.

According to the invention the dye-containing mass comprises a compound of the following formula I:

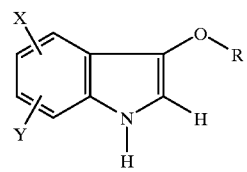

wherein R represents a DL-, D- or L-aldopyranose or a DL-, D- or L-ketopyranose and X and Y, independently of each other, each represent a hydrogen atom, a halogen atom (especially chlorine, bromine or iodine), a hydroxy group or an alkoxy group with from 1 to 4 carbon atoms.

The preferred compound of formula I is the 5-bromo-4-chloro-3-indolyl-β-D-galactoside.

For optimizing the dyeing results and for making special dye effects at least one additional direct-dyeing dye compound, which can, for example, be selected from the group consisting of aromatic nitro dye compounds, azo dye compounds, anthraquinone dye compounds and triphenylmethane dye compounds, alone or mixed with each other, is added to the dye-containing mass.

For example, suitable nitro dye compounds include picramic acid, 4-(2',3'-dihydroxypropyl)amino-3-nitro-trifluoromethylbenzene, 4,N-ethyl-N-(2'-hydroxyethyl)amino-1-(2'-hydroxyethyl)amino-2-nitrobenzene, 2-chloro-6-ethyl-amino-4-nitrophenol, 1-hydroxy-2-β-hydroxyethylamino-4,6-dinitrobenzene, 4-(2'-hydroxyethyl)amino-3-nitrochloro-benzene, 2-amino-6-chloro-4-nitrophenol and 4-(2'-hydroxy-ethyl)amino-3-nitro-methylbenzene.

The azo dye compounds used in the dye-containing mass according to the invention can include, for example, 1-(2'-methoxy-phenylazo)-2-hydroxy-7-trimethylammonium naphthalene chloride (Basic Red 76), 4-(4'-sulfo-1-phenylazo)-1-(4"-sulfophenyl)-3-carboxy-5-hydroxypyrazolone(Acid Yellow 23), 4-amino-4'-bis-(2"-hydroxyethyl)amino-azobenzene (Disperse Black 9) and 1-(4'-aminophenylazo)-2-hydroxy-7-trimethyl-ammonium naphthalene chloride (Basic Brown 16).

The anthraquinone dye compounds used in the present invention can include, for example, 1-methylamino-4-(2'-hydroxyethyl)aminoanthraquinone (Disperse Blue 3), 1-amino-4-hydroxyanthraquinone (Disperse Red 15), 2-methoxy-1,4-diaminoanthraquinone (Disperse Red 11), 1,4-diaminoanthraquinone (Disperse Violet 1), 1-amino-4-methylaminoanthraquinone (Disperse Violet 4), 1,4-bis(2',3'-dihydroxypropyl)aminoanthraquinone, 1-methylamino-4-(amino-n-propyltrimethylammonium)anthraquinone methylsulfate (Basic Blue 22),1,4-bis-(2-hydroxyethyl)amino-5,8-dihydroxyanthraquinone (Disperse Blue 7) and 1-methylamino-4-aminopropylaminoanthraquinone (HC Blue 8).

The triphenylmethane dye compounds used in the invention can include, for example, [4-[[4-diethylamino]-phenyl][4-(ethylamino)-1-naphthalenyl]methylene]-2,5-cyclohexadien-1-yliden]-N-ethylethaneamine(Basic Blue 7) and 4',4',4"-triamino-3-methyltriphenylcarbenium chloride (Basic Violet 14, Fuchsin AN).

The dye-containing mass according to the invention preferably contains from 0.01 to 5 percent by weight of the direct-dyeing dye compounds when they are present, especially from 0.1 to 4 percent by weight.

The dye-containing mass for dyeing keratin fibers according to the invention can consist of the compound of formula I, if necessary in a mixture with one or more of the above-described direct-dyeing dye compounds. The dye-containing mass for dyeing keratin fibers can also comprise the compound of formula I and a suitable cosmetic carrier. In this latter case the dye-containing mass according to the invention for dyeing keratin fibers contains from about 0.001 to 10 percent by weight, especially from 0.1 to 5 percent by weight, of the compound of formula (I).

The dye-containing mass according to the invention produces a blue color in keratin fibers in the presence of air when acted on by an enzyme. This blue color has a satisfactory stability to cosmetic treatments, perspiration and action of light and weather. Furthermore hair is dyed very uniformly and intensively, without leaving a water-insoluble residue on it.

The subject matter of the invention thus also concerns a composition or agent for dyeing keratin fibers, especially hair, which is made by mixing the dye-containing mass with a suitable enzyme immediately prior to use.

The form of the dye-containing mass and the ready-to-use dye composition can, for example, be a solution, especially an aqueous or aqueous-alcoholic solution. The form which is particularly preferred for the composition of the invention is however a cream, a gel or an emulsion and, in the case of the dye-containing or dye-carrying mass, a powder or granulate. The composition contains a mixture of the dye compound ingredients with at least one cosmetic additive ingredient which is conventionally used in this type of composition.

The conventional cosmetic additive ingredients used in the composition according to the invention can include, for example, solvents, such as water; lower aliphatic monovalent or polyvalent alcohols, their esters and ethers, especially alkanols, particularly with 1 to 4 carbon atoms in their alkyl chain, especially ethanol, n-propanol or isopropanol, butanol, isobutanol; di- or trivalent alcohols, especially those with 2 to 6 carbon atoms, for example ethylene glycol, propylene glycol, 1,3-propandiol, 1,4-butandiol, 1,5-pentandiol, 1,6-hexandiol, 1,2,6-hexantriol, glycerol, diethylene glycol, dipropylene glycol, polyalkylene glycols, such as triethylene glycol, polyethylene glycol, tripropylene glycol and polypropylene glycol; lower alkyl ethers of polyvalent alcohols, such as ethylene glycol monomethylether, ethylene glycol monoethylether, ethylene glycol inonopropylether or ethylene glycol monobutylether, diethylene glycol monomethylether or diethylene glycol monoethylether, triethylene glycol monomethylether or triethylene glycol monoethylether; ketones and ketoalcohols, especially those with 3 to 7 carbon atoms in the molecule, especially acetone, methylethylketone, diethylketone, methyl isobutylketone, methylphenylketone, cyclopentanone, cyclohexanone and diacetone alcohol; ethers, such as dibutyl ether, tetrahydrofuran, dioxan or diisopropyl ether; esters, such as ethyl formate, methyl formate, methyl acetate, ethyl acetate, propyl acetate, butyl acetate, phenyl acetate, ethylene glycol monoethylether acetate or acetic acid hydroxyethyl ester; amides, such as dimethylformamide, dimethylacetamide or N-methylpyrrolidone; and urea, tetramethylurea and thiodiglycol; also wetting agents or emulsifiers from the classes of anioric, cationic, amphoteric, nonionic or zwitterionic surface-active substances, such as fatty alcohol sulfates, alkylsulfonates, alkylbenzenesulfonates, alkyltrimethylammonium salts, alkylbetaines, α-olefin sulfonate, ethoxylated fatty alcohols, ethoxylated nonylphenols, fatty acid alkanol amines, ethoxylated fatty acid esters, fatty alcohol polyglycolether sulfates, alkylpolyglucodides; thickeners, such as higher fatty alcohols, starches, cellulose derivative compounds, petrolatum (Vaseline®), paraffin oil, fatty acids and other fat components in emulsion form; water soluble polymeric thickeners, such as natural gums, guar gum, xanthan gum, carob bean core material, pectin, dextran, agar-agar, amylose, amylopectin, dextrine, clay or completely synthetic hydrocolloids, such as polyvinyl alcohol; also care materials, such as lanolin derivatives, cholesterol, pantothenic acid, water-soluble cationic polymers, protein derivative compounds, pro-vitamins, vitamins, plant extracts, sugar and betaine; auxiliary materials, such as electrolytes, antioxidants, fatty amides, sequestering agents, film-forming agents and preservatives.

The above-described ingredients are used in amounts suitable for their individual purposes, for example, the wetting agents and emulsifiers are used in a concentration of about 0.5 to 30 percent by weight (in relation to the dye-containing mass), the thickeners in an amount of about 0.1 to 25 percent by weight (in relation to the dye-containing mass), and the care substances in a concentration of about 0.1 to 5.0 percent by weight (in relation to the dye-containing mass).

To prepare the composition for dyeing keratin fibers according to the invention the dye-containing mass or substance according to the invention is mixed with a suitable enzyme in a solid or liquid form. It is understandably also possible to use solutions and/or suspensions or emulsions of the above-described enzyme in water or an aliphatic mono- or multivalent alcohol, such as ethanol, isopropanol or butanol. Similarly it is also possible to make the composition according to the invention by mixing the dye-containing mass according to the invention which consists of the compound of formula I and, if necessary, at least one direct-dyeing dye compound, with a preparation which contains the above-described enzyme and all the required additional cosmetic additive ingredients.

A hydrolase which catalyzes a hydrolytic cleavage of the compound of formula I is suitable as the enzyme.

Galactosidases, especially β-galactosidase, however are particularly preferred as the enzyme.

The hair dye composition according to the invention advantageously has a pH of from 8 to 11.

In the method for dyeing hair according to the invention a sufficient amount, according to the amount of hair being dyed, usually about 10 to 60 g, of the ready-to-use dye composition for the treatment is applied to the hair. Usually one allows the mixture to act on the hair for about 10 to 45 minutes, preferably for 30 to 40 minutes, at about 15 to 50° C., then rinses the hair with water and dries it. If necessary in connection with the rinsing the hair is washed with a shampoo and/or after-rinsed with a weak organic acid, such as citric acid, glycolic acid, lactic acid, malic acid, ascorbic acid or tartaric acid. Subsequently the hair is dried.

The hair dye composition according to the invention produces dyed hair with outstanding color fastness properties, especially concerning light-fastness, wash-fastness and friction-fastness. According to the type and concentration of compounds of the formula (I) different color shades from bright blue to turquoise, blue, blue-violet to purple can be obtained with the method according to the invention. The exceptional color purity and great color intensity obtained with the composition for dyeing according to the invention are particularly noteworthy. Finally the hair dye composition according to the invention dyes grey and chemically not pre-damaged hair without problems and with very good color coverage. The dyes colors obtained are, independently of the different hair structure, uniformly and very satisfactorily reproduced. A broad palette of color shades and nuances of fashionable red to brown shades can be obtained on addition of further direct-dyeing dye compounds.

The following examples further illustrate the invention in more detail, but they should not be construed as further limiting the claims appended hereinbelow.

EXAMPLES

Example 1: Hair Dye Composition

| | |
|---|---|
| 0.1 g | 5-bromo-4-chloro-3-indolyl-β-D-galactoside, (98%; $[\alpha]_D^{20} = 62°$ (c = 1 in dimethylformamide/water 1:1)) |
| 0.3 g | hydroxyethylcellulose |
| 0.1 g | disodiummethylenediaminotetraacetate hydrate |
| 99.5 g | phosphate buffer, 0.1 m (mixture of potassium dihydrogen phosphate and dipotassium hydrogen phosphate in water; at pH = 7.8) |
| 100.0 g | |

The above-described dye-containing mass is mixed with 1 mg of β-galactosidase (from E. Coli, 380 U/mg at pH=7.8 and 37° C.) immediately prior to use to form the ready-to-use hair dye composition.

Bleached hair then is treated with this ready-to-use hair dye composition for 40 minutes at a temperature of 40° C. Then the hair is rinsed with water, washed with a shampoo as needed and rinsed again with water, and dried. The dyed hair is a light blue color.

The dyed hair retains its color without noticeable intensity loss for up to ten hair washings.

Example 2: Hair Dye Composition

| | |
|---|---|
| 0.1 g | 5-bromo-4-chloro-3-indolyl-β-D-glucopyranoside (99%) |
| 0.3 g | hydroxyethylcellulose(Tylose, water-soluble -- MHB 10,000 P) |
| 0.1 g | disodiummethylenediaminotetraacetate hydrate |
| 99.5 g | phosphate buffer, 0.1 m (mixture of potassium dihydrogen phosphate and dipotassium hydrogen phosphate in water; at pH = 7.8) |
| 100.0 g | |

The above-described dye-containing mass is mixed with 1 mg of β-glucooxidase (from almond, 6.2 U/mg at pH=5 and 35° C.) immediately prior to use to form the ready-to-use hair dye composition.

Bleached hair then is treated with this ready-to-use hair dye composition for 40 minutes at a temperature of 40° C. Then the hair is rinsed with water, washed with a shampoo as needed and rinsed again with water and dried. The dyed hair is a violet blue color.

The dyed hair retains its color without noticeable intensity loss for several hair washings.

Example 3: Hair Dye Composition

| | |
|---|---|
| 0.1 g | 5-bromo-6-chloro-3-indolyl-β-D-galactoside, (98%; $[\alpha]_D^{20} = 46°$ (c = 1 in methanol)) |
| 0.3 g | hydroxyethylcellulose(Tylose, water-soluble -- MHB 10,000 P) |
| 0.1 g | disodiummethylenediaminotetraacetate hydrate |
| 99.5 g | phosphate buffer, 0.1 m (mixture of potassium dihydrogen phosphate and dipotassium hydrogen phosphate in water; at pH = 7.8) |
| 100.0 g | |

The above-described dye-containing mass is mixed with 1 mg of β-galactosidase (from E. Coli, 380 U/mg at pH=7.8 and 37° C.) immediately prior to use to form the ready-to-use hair dye composition.

Bleached hair then is treated with this ready-to-use hair dye composition for 40 minutes at a temperature of 40° C. Then the hair is rinsed with water, washed with a shampoo as needed and rinsed again with water and dried. The dyed hair is a violet to deep blue color.

The dyed hair retains its color without noticeable intensity loss for several hair washings.

1U (=1 international unit) is a unit of enzyme activity. An enzyme preparation having 1 U of activity hydrolyses 1 micromole of glycoside per minute at the given pH and temperature.

All percentages unless otherwise indicated are by weight.

The disclosure in German Patent Application 196 48 019.1 of Nov. 20, 1996 is incorporated here by reference. This German Patent Application describes the invention described hereinabove and claimed in the claims appended hereininbelow and provides the basis for a claim of priority for the instant invention under 35 U.S.C. 119.

While the invention has been illustrated and described as embodied in a dye-containing mass, composition containing it and method for dyeing keratin fibers, especially human hair, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims:

1. A dye-containing mass comprising a cosmetic carrier and from 0.001 to 10 percent by weight of 5-bromo-4-chloro-3-indolyl-β-D-galactoside.

2. The dye-containing mass as defined in claim 1, wherein said cosmetic carrier comprises at least one cosmetic additive ingredient.

3. The dye-containing mass as defined in claim 1, consisting only of said cosmetic carrier and said 5-bromo-4-chloro-3-indolyl-β-D-galactoside.

4. The dye-containing mass as defined in claim 2, further comprising at least one direct-dyeing dye compound.

5. The dye-containing mass as defined in claim 4, wherein said at least one direct-dyeing dye compound is selected from the group consisting of nitro dye compounds, azo dye compounds, anthraquinone dye compounds and triphenylmethane dye compounds.

6. The dye-containing mass as defined in claim 4, wherein said at least one direct-dyeing dye compound is selected from the group consisting of picramic acid, 4-(2',3'-dihydroxypropyl)amino-3-nitrotrifluoromethylbenzene, 4,N-ethyl-N-(2'-hydroxyethyl)amino-1-(2'-hydroxyethyl) amino-2-nitrobenzene, 2-chloro-6-ethyl-amino-4-nitrophenol, 1-hydroxy-2-β-hydroxyethylamino-4,6-dinitrobenzene, 4-(2'-hydroxyethyl)amino-3-nitrochlorobenzene, 2-amino-6-chloro-4-nitrophenol, 4-(2'-hydroxyethyl)amino-3-nitromethylbenzene, 1-(2'-methoxyphenylazo)-2-hydroxy-7-trimethylammonium naphthalene chloride, 4-(4'-sulfo-1-phenylazo)-1-(4"-sulfophenyl)-3-carboxy-5-hydroxypyrazolone, 4-amino-4'-bis-(2"-hydroxyethyl)aminoazobenzene, 1-(4'-aminophenyl-azo)-2-hydroxy-7-trimethylammonium naphthalene chloride, 1-methyl-amino-4-(2'-hydroxyethyl) aminoanthraquinone, 1-amino-4-hydroxyanthraquinone, 2-methoxy-1,4-diamino-anthraquinone, 1,4-diaminoanthraquinone, 1-amino-4-methylamino-anthraquinone, 1,4-bis(2',3'-dihydroxypropyl)-amino-anthraquinone, 1-methylamino-4-(amino-n-propyl-trimethyl-ammonium)anthraquinone methylsulfate, 1,4-bis-(2-hydroxy-ethyl)amino-5,8-dihydroxyanthraquinone, 1-methyl-amino-4-amino-propylaminoanthraquinone, [4-[[4-diethyl-amino]-phenyl]-[4-(ethylamino)-1-naphthalenyl]methylene]-2,5-cyclohexadien-1-yliden]-N-ethylethaneamine and 4',4',4"-triamino-3-methyltriphenylcarbenium chloride.

7. A hair dye composition made by mixing, immediately prior to use, a hydrolase enzyme together with a dye-containing mass containing a compound of formula I:

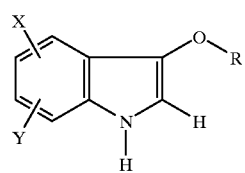

(I)

wherein R represents a DL-, D- or L-aldopyranose or a DL-, D- or L-ketopyranose, and X and Y, independently of each other, each represent a hydrogen atom, a halogen atom, a hydroxy group or an alkoxy group with from 1 to 4 carbon atoms.

8. The hair dye composition as defined in claim 7, wherein said hydrolase enzyme comprises a galactosidase.

9. The hair dye composition as defined in claim 7, wherein said hydrolase enzyme is a β-galactosidase.

10. The hair dye composition as defined in claim 7, having a pH of from 8 to 11.

11. A method of dyeing hair, said method comprising the steps of:

a) providing a hair dye composition made, immediately prior to use, by mixing a hydrolase enzyme with a dye-containing mass containing a compound of formula I:

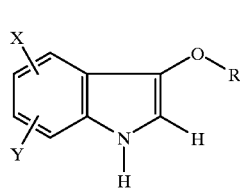

(I)

wherein R represents a DL-, D- or L-aldopyranose and/or a DL-, D- or L-ketopyranose, and X and Y, independently of each other, each represent a hydrogen atom, a halogen atom, a hydroxy group or an alkoxy group with from 1 to 4 carbon atoms;

b) applying said hair dye composition to hair to be dyed;

c) allowing said hair dye composition to act on the hair for 10 to 45 minutes at a temperature of from 15 to 50° C.; and then d) rinsing the hair with water and then drying the hair.

12. The method as defined in claim 11, further comprising shampooing the hair after the allowing of the hair dye composition to act on the hair.

* * * * *